United States Patent [19]
Hutchins

[11] 4,117,842
[45] Oct. 3, 1978

[54] TREATMENT OF CONJUNCTIVITIS WITH POWDERED ALUMINUM AND EYE PROTECTOR/APPLICATOR

[76] Inventor: Frank Hutchins, P.O. Box 9035, 67 Pinedale Rd., Asheville, N.C. 28805

[21] Appl. No.: 771,645

[22] Filed: Feb. 24, 1977

[51] Int. Cl.² ............................................. A61F 13/12
[52] U.S. Cl. .................................... 128/163; 128/260; 424/154
[58] Field of Search .................. 128/163, 132 R, 154, 128/260, 261, 265; 424/154

[56] References Cited

U.S. PATENT DOCUMENTS

| | | | |
|---|---|---|---|
| 3,092,103 | 6/1963 | Mower | 128/163 X |
| 3,098,790 | 7/1963 | Mettentleiter | 424/154 |
| 3,302,646 | 2/1967 | Behney | 128/260 |
| 3,485,244 | 12/1969 | Rosen | 128/260 X |
| 3,952,735 | 4/1976 | Wirtschafter et al. | 128/163 |
| 3,973,561 | 8/1976 | Kane | 128/132 R |

FOREIGN PATENT DOCUMENTS 1,914,096  10/1970  Fed. Rep. of Germany .......... 128/154

*Primary Examiner*—John D. Yasko
*Attorney, Agent, or Firm*—Berman, Aisenberg & Platt

[57] ABSTRACT

Powdered aluminum aids in the treatment of, the alleviation of suffering during and the relief from conjunctivitis. When administered to the eye of an animal afflicted with croupous or membranous conjunctivitis, powdered aluminum assists in breaking down and removing the milky film associated with this malady. The powdered aluminum may be applied to a diseased eye by direct application, by spray or by an eye protector which may be tinted to further assist in the treatment of conjunctivitis by shutting out sun's and other light rays from the afflicted eye.

The powdered aluminum is administered as such or in admixture with boric acid and/or antibiotic.

35 Claims, 4 Drawing Figures

TREATMENT OF CONJUNCTIVITIS WITH POWDERED ALUMINUM AND EYE PROTECTOR/APPLICATOR

BACKGROUND

Conjunctivitis is a generic term relating to inflammation of the conjunctiva. The inflammation can have one or more of numerous causes, such as trauma, infection and allergy, and is in no way limited to afflicting humans. In fact, particular concern with regard to this disorder is in connection with cattle and horses affected thereby.

Sun rays and other actinic radiation are harmful to diseased eyes and impede or prevent curing, healing or obtaining relief from conjunctivitis. It is thus advantageous to block such rays so that they do not reach eyes of subjects afflicted with conjunctivitis.

According to U.S. Pat. No. 3,098,790 powdered aluminum is useful for treating and healing open wounds. Administration by dusting and spraying is also reported in this patent.

SUMMARY OF THE INVENTION

Powdered aluminum assists in treating, obtaining relief from and curing conjunctivitis, particularly membranous or croupous conjunctivitis, but also other forms, such as actinic and acute contageous conjunctivitis. In addition to impeding the passage of sun rays into an eye sprayed or otherwise treated with powdered aluminum, such aluminum, e.g. in micronized form, breaks up and/or removes the white milky film characteristic of membranous or croupous conjunctivitis.

By combining the powdered aluminum with a minor proportion of boric acid, a particularly advantageous composition results. The boric acid cooperates with the powdered aluminum and assists in removing all foreign matter, including the residue of the broken down milky film, from the affected eye to which the composition has been applied. The powdered aluminum appears to act as a cutting agent with regard to the white milky film, which it removes from the eye. When the admixture is sprayed into an eye of an afflicted host, it cuts away the film and is washed from the eye with the film residue by normal tear action.

A minor proportion of an antibiotic is also advantageously combined with the powdered aluminum. Not only does such antibiotic impede or prevent further infection, it acts positively in the treatment of conjunctivitis when the latter is caused or aggravated by a microorganism.

The powdered aluminum, either alone or with boric acid and/or an antibiotic, may be applied to the diseased eye of the animal via an eye protector in the preferred form of a curved lens having an amount of the curing agent predisposed thereon. The lens is preferably tinted to further assist in shielding the afflicted eye from harmful outside radiation. The lens, which may be of any suitable shape so as to cover the eye, also preferably includes means for ventilating the eye, and means for permitting the eye to drain. The ventilating and drainage means, in a preferred form, each are embodied by a wire screen mesh preferably formed at the lower portion of the lens of a rust-proof material. The lens structure also preferably includes means for conveniently mounting same about the afflicted eye. The eye protector may be utilized in treating conjunctivitis either alone or in combination with the powdered aluminum or compounds thereof.

BRIEF DESCRIPTION OF THE DRAWINGS

The features and advantages of the present invention outlined above will become better understood from the following detailed description of the present invention considered partly in connection with the accompanying drawings, in which.

DETAILED DESCRIPTION OF THE INVENTION

Figure 1:
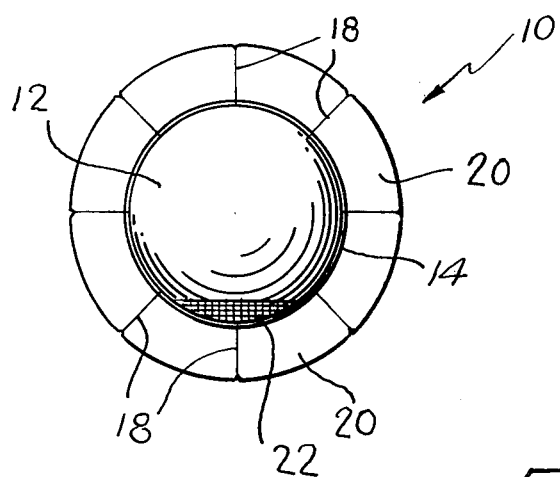
FIG. 1 is a front, plan view of a preferred embodiment of an eye protector/applicator of the present invention.
Figure 2:
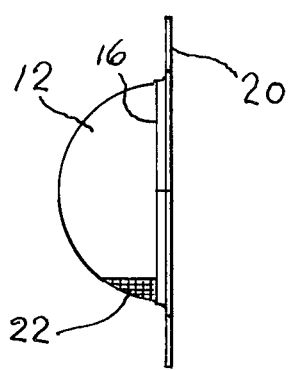
FIG. 2 is a side view of the preferred embodiment illustrated in FIG. 1.
Figure 3:
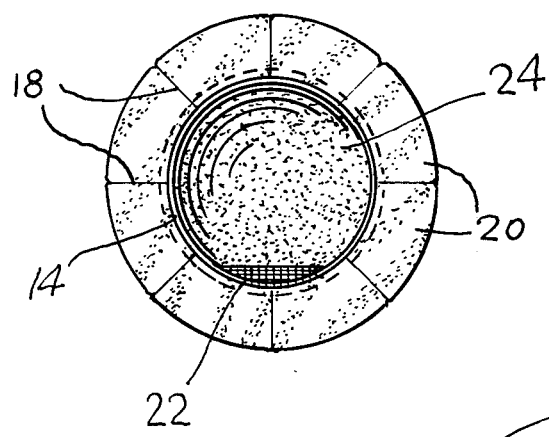
FIG. 3 is a rear, plan view illustrating the preferred embodiment shown in FIG. 1 and having powdered aluminum sprayed thereon.

Aluminum is commercially available in powder form, and such form is suitable for the use contemplated by this invention. The powdered aluminum must naturally be sufficiently sterile or contaminant free to be pharmacologically acceptable for administration to the surface of an eye.

The powdered or pulverized aluminum is of any suitable particle-size range, e.g. of 20 microns or smaller. When it has such a particle-size range, it is regarded as micronized aluminum. It is optionally of any particle-size range suitable for the practice of the invention disclosed in U.S. Pat. No. 3,098.790.

In treating conjunctivitis, powdered aluminum is applied to an eye surface either by itself or in combination with one or more other ingredients. In any resulting compositions the powdered aluminum should be the predominant component. Boric acid is advantageously admixed with the powdered aluminum and works with the powdered aluminum to assist in dispelling broken down white milky film and other foreign matter from the eye. Whenever tissue is inflamed, it is more subject to infection. By incorporating an antibiotic with the powdered aluminum, such infection may be warded off. As infection is also one cause of conjunctivitis, an antibiotic is also useful in treating and curing such conjunctivitis.

Compositions useful for administering to eyes of subjects, e.g. horses and cattle, afflicted with conjunctivitis comprise powdered aluminum predominantly or exclusively. (They are dry compositions which are free from, or at least have no requirement for the presence of vegetable gum.) Such compositions optionally comprise up to about 20 percent by weight of boric acid and up to about 20 percent by weight of antibiotic, e.g. neomycin. Preferred compositions contain about 10 percent by weight of boric acid and about 10 percent by weight of neomycin; they are in the form of a sprayable powder suitable for spraying directly onto the surface of an affected eye. (Suitable spraying means are known and do not constitute part of this invention.)

The compositions used for this invention need not be administered by spraying onto an eye surface; they are optionally applied, e.g., from a squeeze bottle directly to such surface in amount of from about 1 to 2 milligrams per application per eye. One particularly advantageous mode of treatment employs an animal-eye protector with a lens heavily coated with such a composition, e.g., by spraying the composition on the inside surface of the lens. As the composition is in powder form and the coated lens is so close to the affected eye, the powder intermittently, e.g. as the head of the animal is moved, goes into the eye over an extended period of time. The eye protector has the added advantage of keeping sun rays from the eye and providing a way to administer the composition to the eye without exposing the eye to actinic radiation. Powdered aluminum also absorbs sun rays and thus further assists in this phase of treatment.

Referring now to FIGS. 1 through 4, a preferred embodiment of a suitable eye protector and applicator for the powdered aluminum is indicated generally by reference numeral 10. Eye protector 10 includes a central lens portion 12 which may be made of either glass or plastic. Lens 12 is preferably tinted so as to further assist in screening out the sun's radiation, and other harmful light, to facilitate the healing process. While the lens 12 is illustrated as being a spherical section, any suitable shape will suffice.

Figure 4:
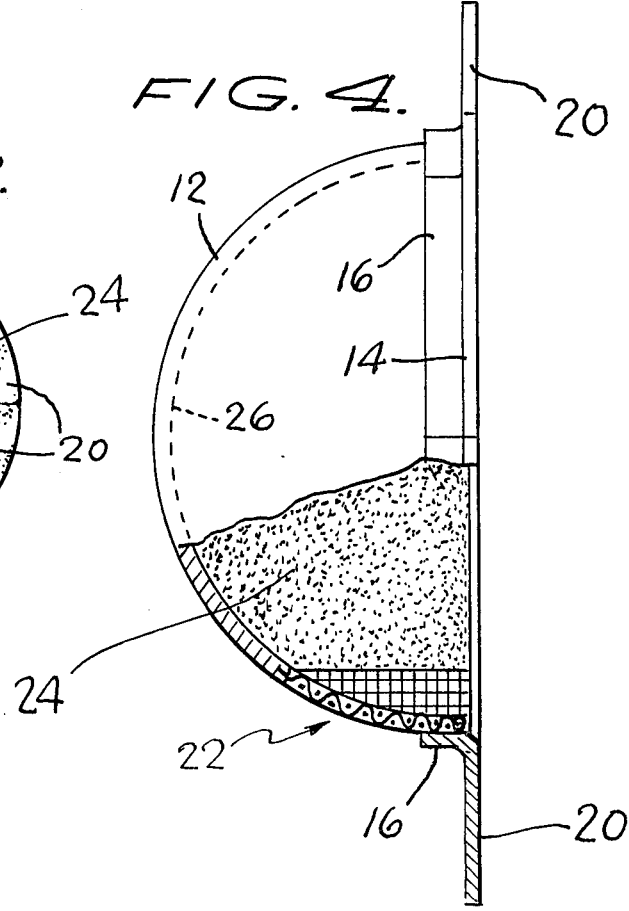
FIG. 4 is an enlarged, side, partially broken and sectional view of the preferred embodiment shown in FIG. 3.

The lens 12 may be mounted in a substantially circular lens holder or base 14 which has a slight upstanding peripheral flange 16 formed thereabout within which the lens 12 may be secured (FIG. 4). Extending radially from the base 14 are a plurality of tangs or prongs 18 which serve as mounting means over which an adhesive tape 20 or the like may be placed when fitting the eye protector 10 over the afflicted eye of the animal. Adhesive tape 20 is preferably weather-proof to permit outdoor, uninterrupted use. In lieu of adhesive-backed tape, a rapid drying, weather-proof glue may be employed. Other equally suitable mounting means will suggest themselves to persons of ordinary skill.

At the lower portion of lens 12 is positioned a wire screen mesh 22 which is preferably formed of a rustproof material, such as plastic. The wire screen mesh 22 serves the dual purpose of ventilating the eye to fresh air and serves as an outlet for possible drainage from the eye. Illustrated in FIGS. 3 and 4 and indicated by reference numeral 24 is the pre-coated micronized aluminum which may be heavily applied to the inner surface 26 of the lens 12 prior to mounting of the eye protector 10 over the afflicted eye. As stated above, while many shapes of lens 12 will be suitable, I have found that one which places the apex of the inner surface 26 within ½ to 1 inch from the surface of the afflicted eye to be particularly advantageous. Clearly, the eye protector 10 may be utilized in its uncoated state as an effective radiation shield for facilitating the healing process.

The provided compositions should be administered to affected eyes as soon as possible after the onset of conjunctivitis. With horses and cattle permanent injury can result from delay. The powdered aluminum or powdered aluminum composition is administered to affected eyes (by spray or by direct application) as often as three times during each 24-hour period until the film is completely removed from the eyes and, perhaps, at a slightly-reduced frequency thereafter until inflammation has completely disappeared. From 1 to 2 milligrams of powdered aluminum are applied to the surface of an affected eye during each administration. This treatment is regarded as the quickest way to remove the white milky film which is characteristic of certain conjunctivitis.

For two-component compositions consisting of powdered aluminum and boric acid, the several ingredients are merely blended together until a uniform and substantially homogeneous dry powder admixture is obtained. For admixtures including an antibiotic, the antibiotic, e.g. neomycin, is first thoroughly blended with the aluminum powder (for about five minutes with quantities of 10 grams of aluminum powder and 1 gram of neomycin). If boric acid is to be incorporated therein, the boric acid is then thoroughly blended with the obtained admixture until a substantially homogeneous and thoroughly dry three-component blended composition is obtained.

Obviously, numerous modifications and variations of the present invention are possible in light of the above teachings. It is therefore to be understood that within the scope of the appended claims, the invention may be practiced otherwise than as specifically described herein.

What is claimed is:

1. A process for administering powdered aluminum to a diseased eye of an animal afflicted with conjunctivitis, which comprises spraying the powdered aluminum on the inner surface of an eye protector and mounting said eye protector to cover without contacting the afflicted eye.

2. A process according to claim 1 which further comprises shielding the afflicted eye from the sun's radiation.

3. An applicator for administering powdered aluminum to a diseased eye of an animal afflicted with conjunctivitis, which comprises means for covering the diseased eye of the animal, said covering means adapted to be spaced from the surface of the eye and having an amount of said powdered aluminum predisposed thereon.

4. An applicator according to claim 3, wherein said covering means comprises a lens.

5. An applicator according to claim 4, wherein said lens includes means for shielding the animal's eye from radiation.

6. An applicator according to claim 5, wherein said shielding means comprises a tint imparted to said lens.

7. An applicator according to claim 4, wherein said covering means further includes means for ventilating the eye of said animal to outside air.

8. An applicator according to claim 4, wherein said covering means further includes means for draining the eye of said animal therethrough.

9. An applicator according to claim 7, wherein said ventilating means comprises an open screen mesh positioned at the lower portion of said lens.

10. An applicator according to claim 8, wherein said drain means comprises an open screen mesh positioned at the lower portion of said lens.

11. An applicator according to claim 4, wherein said lens includes means for mounting same about the afflicted eye of the animal.

12. An applicator according to claim 11, wherein said mounting means includes a base for supporting said lens, a plurality of tangs radially extending from said base, and adhesive means for attaching said tangs about the eye of said animal.

13. An applicator according to claim 4, wherein said lens is formed of glass.

14. An applicator according to claim 4, wherein said lens is formed of plastic.

15. An eye protector which comprises a tinted lens adapted for mounting about an afflicted eye of an animal, for preventing the sun's harmful radiation from reaching the afflicted eye and including open screen mesh means positioned at the lower portion of said lens for allowing air ventilation of said eye and for permitting said eye to drain through said eye protector.

16. An eye protector as set forth in claim 15, wherein said lens is coated on its inner surface with powdered aluminum prior to mounting same about said eye.

17. An animal eye protector which comprises means for covering without contacting a diseased eye of said animal to prevent outside radiation from reaching said diseased eye and medication comprising powdered aluminum contained within said covering means.

18. An animal eye protector as set forth in claim 17, wherein said covering means comprises a lens.

19. An animal eye protector as set forth in claim 18, wherein said lens includes means for shielding the animal's eye from radiation.

20. An animal eye protector as set forth in claim 19, wherein said shielding means comprises a tint imparted to said lens.

21. An animal eye protector as set forth in claim 18, wherein said covering means further includes means for ventilating the eye of said animal to outside air.

22. An animal eye protector as set forth in claim 18, wherein said covering means further includes means for draining the eye of said animal therethrough.

23. An animal eye protector as set forth in claim 21, wherein said ventilating means comprises an open screen mesh positioned at the lower portion of said lens.

24. An animal eye protector as set forth in claim 22, wherein said drain means comprises an open screen mesh positioned at the lower portion of said lens.

25. An animal eye protector as set forth in claim 18, wherein said lens includes means for mounting same about the afflicted eye of the animal.

26. An animal eye protector as set forth in claim 25, wherein said mounting means includes a base for supporting said lens, a plurality of tangs radially extending from said base, and adhesive means for attaching said tangs about the eye of said animal.

27. An animal eye protector as set forth in claim 18, wherein said lens is formed of glass.

28. An animal eye protector as set forth in claim 18, wherein said lens is formed of plastic.

29. An animal eye protector as set forth in claim 18, wherein said powdered aluminum is coated on the inner surface of said lens.

30. A process according to claim 1, further comprising boric acid and/or antibiotic admixed with said powdered aluminum.

31. An applicator according to claim 3, further comprising boric acid and/or antibiotic admixed with said powdered aluminum.

32. A protector/applicator for treating a diseased eye of an animal afflicted with conjunctivitis which is characterized by the formation of a white, milky film over the diseased eye, which comprises means for covering without contacting said diseased eye, and medication means predisposed in said covering means for breaking down said white, milky film.

33. The protector/applicator as set forth in claim 32, wherein said medication means comprises powdered aluminum.

34. The protector/applicator as set forth in claim 33, wherein said medication means further comprises boric acid.

35. The protector/applicator as set forth in claim 34, wherein said medication means further comprises an antibiotic.

* * * * *

UNITED STATES PATENT AND TRADEMARK OFFICE
CERTIFICATE OF CORRECTION

PATENT NO. : 4,117,842

DATED : October 3, 1978

INVENTOR(S) : Frank Hutchins

It is certified that error appears in the above—identified patent and that said Letters Patent are hereby corrected as shown below:

In the title, line 2, "POWDERED" should read --MICRONIZED--.

Signed and Sealed this

Twentieth Day of February 1979

[SEAL]

Attest:

RUTH C. MASON
*Attesting Officer*

DONALD W. BANNER
*Commissioner of Patents and Trademarks*